United States Patent [19]
Brendling

[11] 4,453,938
[45] Jun. 12, 1984

[54] URINE COLLECTING INCONTINENCE GUARD

[75] Inventor: Lennart I. Brendling, Järfälla, Sweden

[73] Assignee: Landstingens Inkopscentral, LIC, Ekonomisk Forening, Solna, Sweden

[21] Appl. No.: 445,144

[22] Filed: Nov. 29, 1982

Related U.S. Application Data

[63] Continuation of Ser. No. 242,900, Mar. 12, 1981, abandoned.

[51] Int. Cl.$^3$ .............................................. A61F 5/44
[52] U.S. Cl. .................................. 604/346; 604/349; 383/907; 383/113
[58] Field of Search .............. 128/295, 272, 275, 760, 128/767, 762, 283, DIG. 24; 4/144.1–144.4, 259, 274, 285; 206/822; 229/53; 150/1; D9/305, 306; 604/317, 322, 327, 328, 329, 331, 262, 346, 347, 349

[56] References Cited

U.S. PATENT DOCUMENTS

| 1,171,431 | 2/1916 | Gorton | 229/53 |
|---|---|---|---|
| 2,819,472 | 1/1958 | Sullivan | 4/144.2 |
| 2,878,486 | 3/1959 | Bartlett et al. | 4/144.4 |
| 3,306,515 | 2/1967 | Beaumont | 4/144.2 |
| 3,403,410 | 10/1968 | Benzel et al. | 4/144.2 |
| 3,452,750 | 7/1969 | Blanford | 128/283 |
| 3,572,318 | 3/1971 | Garland | 4/144.3 |
| 3,724,461 | 4/1973 | Eisenberg | 128/275 |
| 4,149,537 | 4/1979 | Haswell | 128/767 |
| 4,197,849 | 4/1980 | Bostick | 128/295 |

FOREIGN PATENT DOCUMENTS 2533016 2/1977 Fed. Rep. of Germany ....... 4/144.1

*Primary Examiner*—C. Fred Rosenbaum
*Assistant Examiner*—J. L. Kruter
*Attorney, Agent, or Firm*—Young & Thompson

[57] ABSTRACT

An incontinence guard for male use comprises a sheath with an insertion opening along one edge and edge portions beside the opening are disposed such that, when the guard is in place, the edge portions are directed obliquely upwards one on each side of the penis root to grip the sides of the penis and improve retention of the guard in position.

1 Claim, 4 Drawing Figures

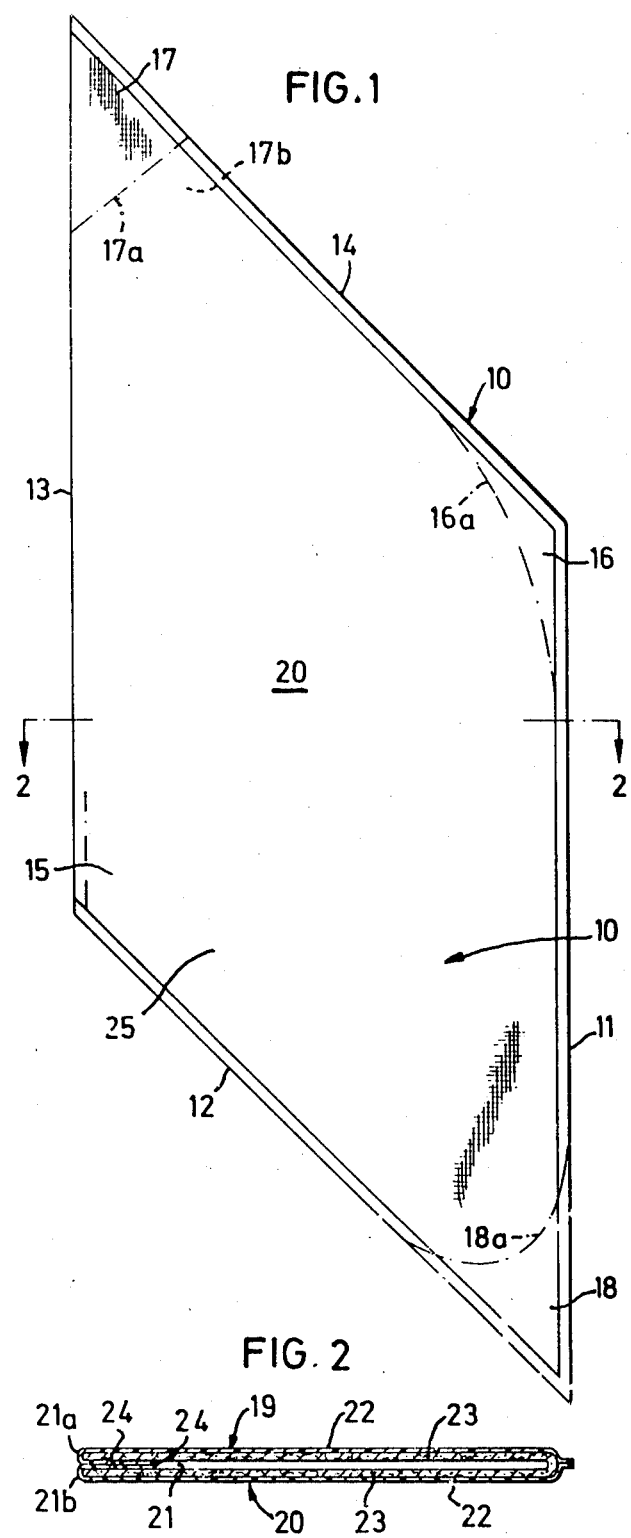

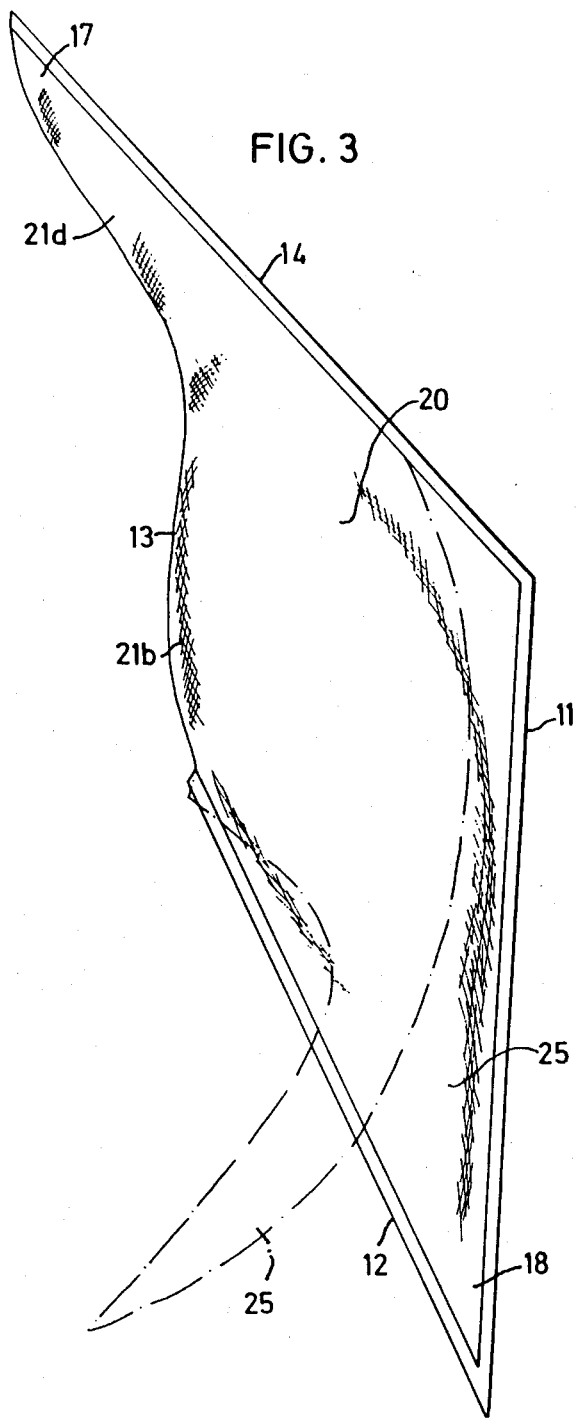

URINE COLLECTING INCONTINENCE GUARD

This application is a continuation of application Ser. No. 242,900, filed Mar. 12, 1981, now abandoned.

The present invention relates to urine-collecting incontinence guards for male use comprising a urine holding sheath having an insertion opening surrounded by an edge portion.

It is known to form such guards as a stocking-shaped sheath with an insertion opening facing upwards, the rear edge of the opening being horizontal and straight when in use. The sheath is formed by back and front walls and the front wall extends upwards above the opening and forms a shield to provide extra protection. For men with normally large penises this form of guard functions satisfactorily. However, if the penis is substantially smaller than the normal size, as is the case in particular with elderly men with a retracted penis condition, the protection provided by such guards is less satisfactory.

The object of the present invention is to provide a urine collecting incontinence guard which can be widely used with the different sizes of penis and penis positions which may be encountered.

According to the present invention, in such a guard which comprises a urine holding sheath having an insertion opening surrounded by an edge portion, the sheath and the opening are so shaped that when, in use, the penis or penis and scrotum of the wearer are inserted through the opening into the sheath, the edge portion grips the penis or penis and scrotum only around a part of the perimeter of the penis or penis and scrotum.

Preferably, the sheath comprises two identical side walls which are united along the edges thereof except for the opening which is in one edge, the edges adjacent the edge in which the opening is formed extending obliquely from the said edge to form a somewhat cone-shaped urine collection pocket below the opening when the guard is in its position of use, and when the guard is in use the side parts of the edge portion extend from the bottom end of the opening obliquely upwards on both sides of the penis or scrotum.

The guard is so formed that in use the edge portion around the insertion opening is situated around the root of the penis and possibly also around the scrotum. The side edge parts of the edge portion extend upwards on both sides of the penis from the bottom end of the opening.

Since parts of the edge portion bounding the opening close tightly against the skin in the area around the penis along the length of the opening edges, leakage of urine from the guard is effectively countered. Below the opening there is the cone-shaped collection pocket which pliably adjusts itself to the body shape and the space between the legs of the wearer. If the penis is of normal size or larger, a good grip is obtained by the opening edges at the bottom end of the opening, these edges being obliquely upwardly directed in their respective directions, as mentioned above. On the other hand, if the penis is of small size or is retracted, urine can be caught by a portion of the guard forming a front shield thereof. This shield extends upwards right up to the upper end of the opening. Even if the penis is obliquely upwardly directed, urine will thus be caught by the guard and retained in it. The guard in accordance with the invention is primarily intended for use in cases of drop incontinence.

Inside the guard, moisture absorbent material is preferably provided. This may comprise a high-absorption material known per se, which has a small volume when in a dry condition and can be arranged in relatively thin layers in the guard, while when it absorbs urine it swells up to form a soft jelly-like and easily deformable mass which conforms practically without resistence to the available space between the legs of the wearer of the guard. The liquid absorbent material can also comprise other known materials such as cellular wadding. In both cases the material is to advantage enveloped in non-woven fabric to prevent the material protruding at the edges of the opening of the guard, when the absorbent material is wet.

The guard may be formed externally of easily flexible plastics film which is preferably folded inwards with edge flaps at the edges of the opening. The flaps extend over the edges of the moisture absorbent material so that, in use, the flaps lie sealingly against the skin to prevent urine running out at the edges of the opening.

Tightly fitting pants are suitably used to retain the guard in position in all conditions, or panties which are specially formed for keeping napkins and sanitary towels in place, as known in the art. The outside of the guard can furthermore have a friction-increasing coating to increase friction against the retaining pants.

An example of a guard in accordance with th invention will now be described with reference to the accompanying drawings in which:

FIG. 1 is a side view of the guard before use;

FIG. 2 is a section along the line 2—2 in FIG. 1;

FIG. 3 is a side view of the guard in a partically opened condition, as it is when in use, inward folding for adjustment to the genitals of the wearer being indicated by chain-dotted lines.

Figure 4:
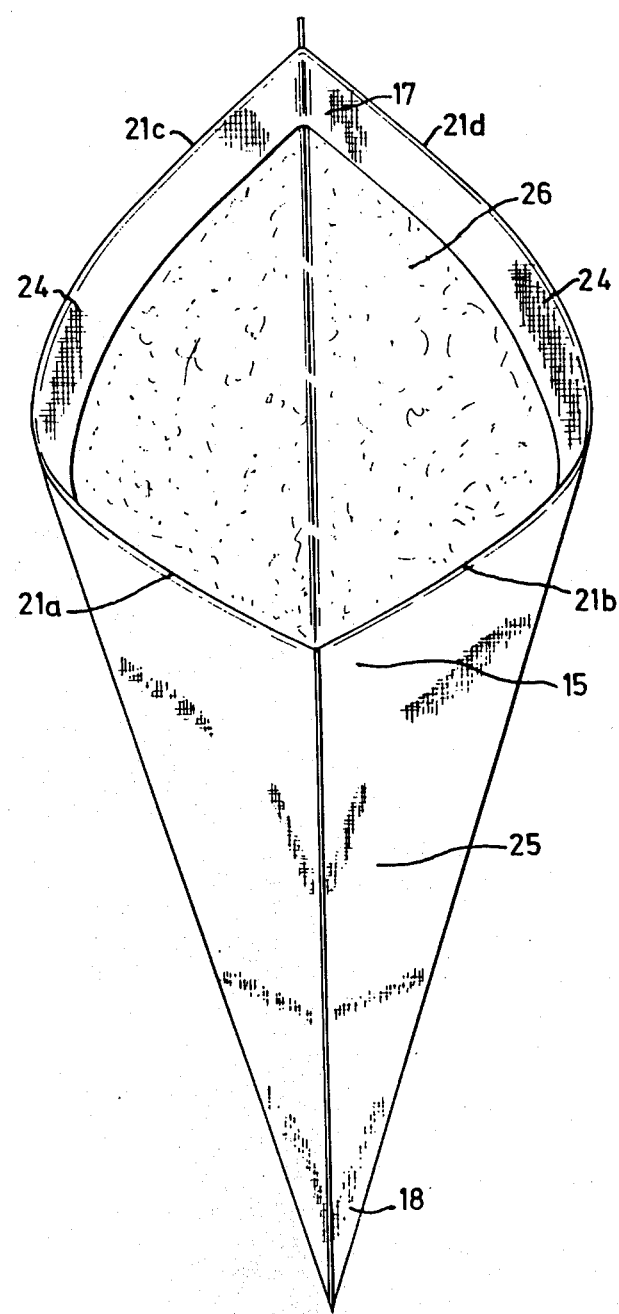
FIG. 4 is a view from the back of the opened guard as seen looking from the left in FIG. 3, showing the shape of the opening of the guard in a configuration which can be varied from person to person.

As is shown in FIGS. 1 and 2, the guard 10 can be manufactured from two plastics sheets cut into pieces with the shape shown and welded together. The edges 11, 12, 13, 14 of the guard form a parallogram having a pair of diagonally opposing acute corners 17, 18.

The complete guard consiss of two similar side walls 19, 20 which are welded to each other at the side edges 11, 12, 14, while the side walls are free of each other at the edge 13 to obtain an insertion opening 21. The edges 11, 13 are somewhat longer than the edges 12, 14 but are shorter than double the length of the edges 12, 14.

As is apparent from FIG. 1, the guard extends from the opening 21 at a downward inclination to the edges of the opening. This results in a shape such that a cone-like pocket 25 is obtained extending below the bottom end of the opening.

Each of the side walls has a liquid-impermeable outer layer 22 formed from the two plastics sheets and an inner liquid absorbent layer 23. The layer 23 is suitably made from high-absorption material which is known per se, but cellular wadding or the like can alternatively be used. On the outside of the absorbent layer 23 there is preferably a layer of non-woven fabric or the like which extends round the edges of the moisture absorbent material to keep this material in position after it has been saturated so that the absorbent layer is prevented from protruding outside the layers 22 through the opening of the guard.

As shown in FIG. 2, the layer 22 is preferably covered by edge flaps 24 at the edges 21a, 21b of the side walls at the opening 21, to prevent urine running out at the edges of the absorbent layer. The edge flaps thus help to avoid both urine and the moisture absorbent material from escaping at the edges of the opening.

The opening 21 does not need to extend along the whole length of the side edge 13, and a portion of this edge can be closed in the vicinity of the obtuse corner 14, as is indicated by a chain-dotted line near the corner 15, particularly if it is desired to increase the volume of the pocket 24 below the corner 15.

Since the guard is made of easily foldable and flexible sheet material it can be deformed into shape as desired when put into place, and when the moisture absorbent layers 23 have been softened by urine, deformation can take place even more easily for adjustment to the available space between the legs of the wearer.

The guard illustrated in FIGS. 1 and 2 can be used effectively regardless of whether the penis has a normal length or is retracted, as is sometimes the case with elderly men. In certain cases the penis length may be very small.

In order to fit the guard in position, it is opened by parting the edges 21a, 21b of the opening to expand the width of the opening 21, e.g. to the shape shown in FIG. 4. At the same time, the area around the obtuse corner 15 is pushed inwards in a direction towards the edge 11. This results in the guard assuming a curved somewhat conical shape of which the lower portion below the obtuse corner 15 forms a relatively capacious cone-shaped collection pocket 25 into which the penis is inserted. As seen from FIG. 4, the side edges 21a, 21b of the opening extend obliquely upwards and outwards to the sides from the obtuse corner 14. This ensures that these portions of the edges of the opening will lie snugly against the root of the penis, or against the scrotum of the wearer if the scrotum is also inserted into the pocket 25, which is sometimes necessary especially if the penis is retracted. In this way improved clamping of the guard under the penis or scrotum is achieved and at the same time the lateral position of the guard is fixed relative to the penis.

By reason of the particular shape of the guard in accordance with the invention, it has a front wall, when in use, in a position in which is forms a shield 26 behind the opening 21 as seen in FIG. 4, that is looking in a direction away from the body of the wearer. The shield 26 tapers upwards to the corner 17, upper parts 21c, 21d of the edges 21a, 21b of the opening extending up to the corner 17.

The shield 26 will intercept drops of urine or a stream of urine from the penis, irrespective of whether the drops or stream are directed upwards, forwards to one side or downwards and the urine will be directed into the pocket 25.

The pocket 25 can be adjusted comfortably into the space between the legs of the wearer and due to its tapering shape it will embarrass the wearer considerably less than if it were of a substantially uniform width along its whole length.

After the guard has been adjusted over the penis, pants are put on to keep the guard in place.

From the point of view of manufacture, it is simplest and most economical to make the guard with all the side edges straight, but the side edges can with advantage be partly curved, having rounded corners at the corners of the guard to improve still further the fit of the guard and make it confortable to wear.

Thus, as shown in FIG. 1, the upper corner can be cut off along a line 17a, and be welded along this line so that an upper collection pocket 17b is obtained. This further increases protection security, especially when the guard is placed over a retracted penis which is directed forwards or upwards.

The corners 16, 17 can also to advantage be smoothly rounded as indicated by the chain dotted lines 16a and 18a.

What I claim is:

1. A urine collecting incontinence guard for male use, comprising a urine holding sheath comprised by two identical side walls which are sealed together along the edges thereof except for an opening which is along one edge, the edges adjacent the edge along which the opening is formed being substantially parallel to each other and extending one at an acute angle and the other at an obtuse angle from said one edge, said side walls each comprising an outer layer of urine-impermeable material and an inner layer of urine-absorbing material, said edge opposite said opening being substantially parallel to said edge in which said opening is formed, said edge along which said opening is formed and its opposite edge being longer than the other two edges, said impermeable material being folded over the inner side of said absorbing material along said edge in which the opening is formed, thereby forming an edge means to minimize the loss of both urine and moisture absorbing material at the edges of the opening.

* * * * *